US00PP14191P29

(12) United States Plant Patent
Westhoff

(10) Patent No.: US PP14,191 P2
(45) Date of Patent: Sep. 30, 2003

(54) VARIETY OF SUTERA PLANT NAMED 'WESBAMEGA'

(50) Latin Name: *Sutera cordata*
Varietal Denomination: 'Wesbamega'

(75) Inventor: Heinrich Westhoff, Fresenhorst 22-24, 46354 Südlohn/Oeding (DE)

(73) Assignees: Heinrich Westhoff (DE); Josef Westhoff (DE)

( * ) Notice: Subject to any disclaimer, the term of this patent is extended or adjusted under 35 U.S.C. 154(b) by 0 days.

(21) Appl. No.: 10/341,964
(22) Filed: Jan. 14, 2003
(51) Int. Cl.[7] ..... A01H 5/00
(52) U.S. Cl. ..... Plt./263
(58) Field of Search ..... Plt./263

*Primary Examiner*—Kent Bell
(74) *Attorney, Agent, or Firm*—Webb Ziesenheim Logsdon Orkin & Hanson, P.C.

(57) ABSTRACT

A new and distinct early flowering Sutera plant with large white colored flowers and vigorous growth.

2 Drawing Sheets

Botanical classification: *Sutera cordata.*
Varietal denomination: 'Wesbamega'.

BACKGROUND OF THE INVENTION

The present invention comprises a new and distinct cultivar of Sutera plant known by the varietal name 'Wesbamega'. The new variety was discovered in 2001 in a selected breeding program in Südlohn, Germany designed to produce a new variety of Sutera with large, white flowers. The new variety was selected from a cross of proprietary unpatented breeding plants Bacopa FA9 (female parent) and Bacopa FA051 (male parent). The new variety has shorter internodes, more uniform petal margins, and improved rooting from cuttings than the female parent with similar leaves, flower color, and flower size. Compared to the male parent, the new variety has larger flowers, larger leaves, darker leaf color, and more branching with similar flower color. The new variety was first asexually reproduced in 2000 by cuttings in Südlohn, Germany. The new variety has been trial and field tested at Südlohn and has been found to retain its distinctive characteristics and remain true to type through successive propagations.

The following traits in combination distinguish 'Wesbamega' as a new and distinct cultivar:

1. Very big flowers.
2. Abundance of flowers.
3. Symmetrical growth, short internodes.
4. Cascading but rounded plant habit, well branched.
5. Very vigorous growth.
6. Attractive clear white colored blossoms with an orange throat.
7. Lateral branches with an optimal diameter for cuttings.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
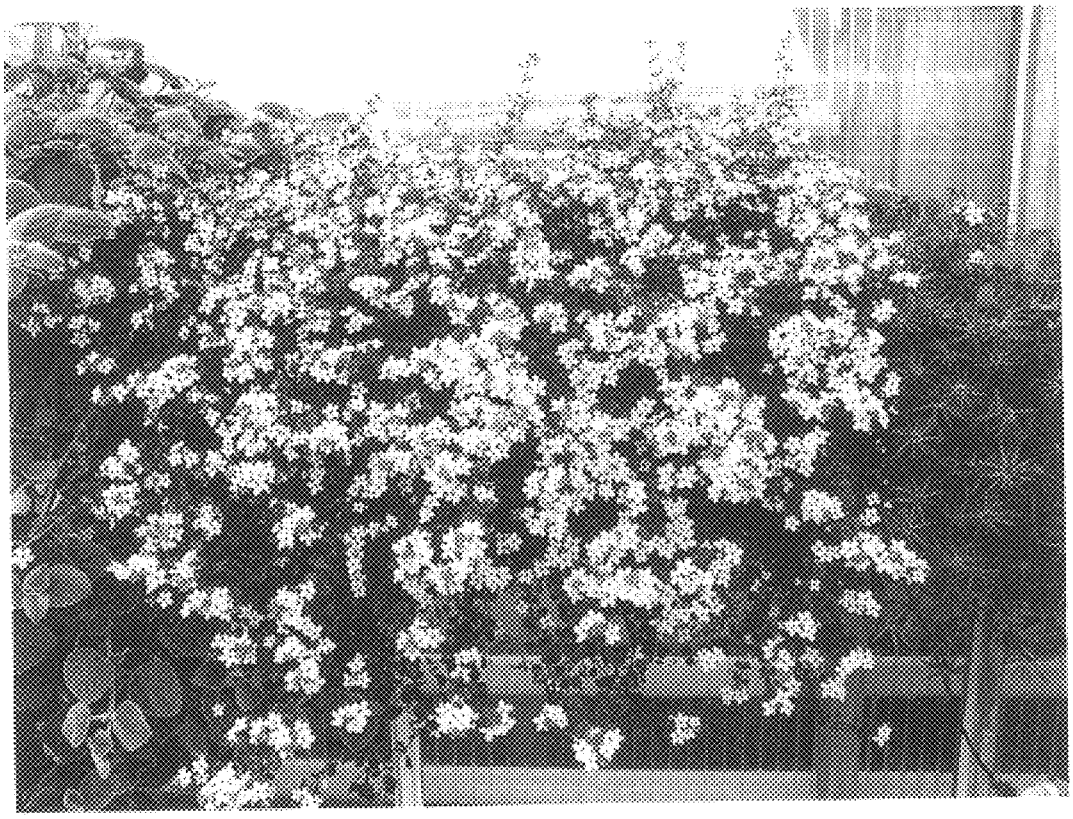
FIG. 1 is a photograph of the plant.
Figure 2:
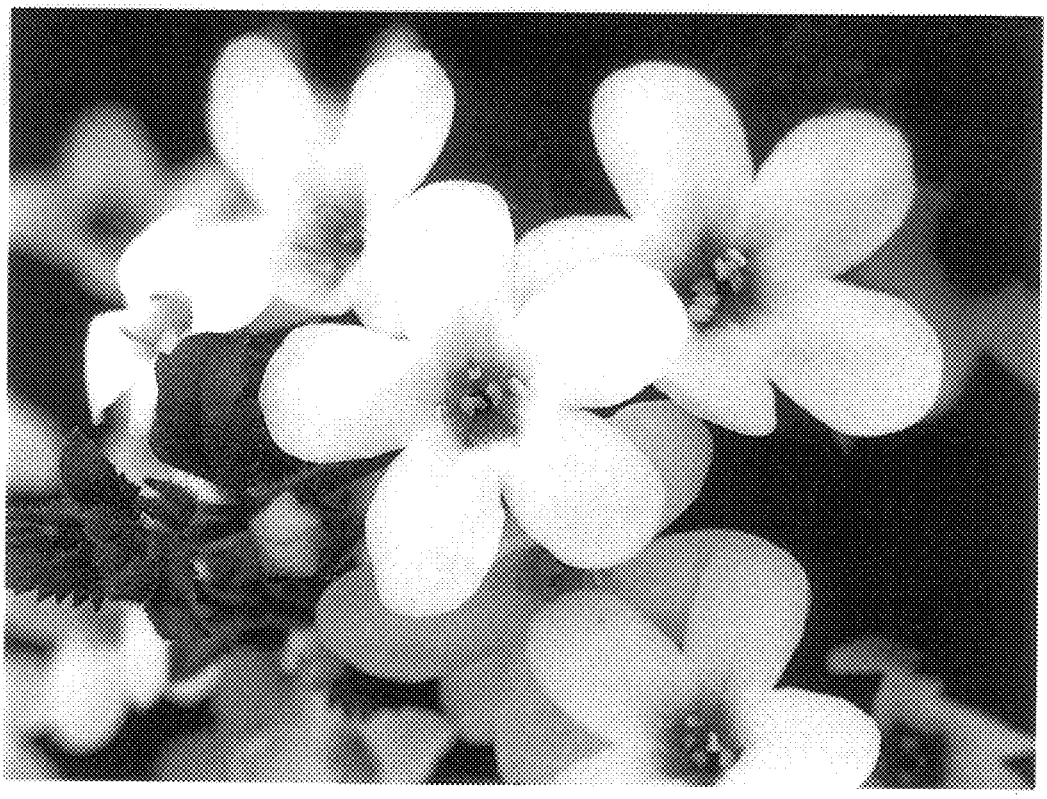
FIG. 2 is a close up view of the blooms of the new plant.

The following detailed description sets forth characteristics of the new cultivar. The data which defines these characteristics were collected by asexual reproductions by cuttings carried out in Südlohn, Germany. Flowering plants were produced in 12–15 weeks without growth retardants and were grown in 12 cm containers with pinching 3–4 weeks after potting. Plants for the description were 20 weeks old, grown in a greenhouse at 20–25° C. daytime temperature and at 16–18° C. night temperature with light levels of 3,000–50,000 lux. The color readings were taken on a plant outdoors and in a greenhouse under natural light. Color references are primarily to the 2001 R.H.S. Colour Chart of The Royal Horticultural Society of London.

Compared to the variety 'Wesbawei' (Co-pending U.S. Plant patent Application Ser. No. 10/037,838), the new variety has larger flowers, shorter internodes, smaller leaves, shorter peduncles, and more orange color of the flower throat. Compared to the unpatented variety 'Sutera Nova', the new variety has larger flowers, shorter internodes, smaller leaves, shorter petioles, deeper orange color of the flower throat, and larger flower buds.

PLANT

Form: Weeping, well branched.
Height: 12–14 cm from soil to top of flowers; 63 cm wide.
Roots:
- *Habit.*—Fine; fibrous, well-branched.
- *Time to initiate roots.*—About 14–16 days at 20° C.
- *Time to produce a rooted cutting or liner.*—About 24–28 days at 20° C.

Main stem: 60 cm long; 2.1 mm diameter; colored 143B; very dense, short, white pubescence.
Branching habit: Generally 2 branches per node at the midpoint of the branch with pinching.
Lateral branches:
- *Diameter.*—1.5 mm.
- *Length.*—15 cm.
- *Internode length.*—1.8 cm.
- *Quantity.*—Abundant.
- *Color.*—143B.

Foliage:
*Arrangement.*—Opposite.
*Size of leaf.*—Length: 2.1 cm. Width: 1.8 cm.
*Shape of leaf.*—Rhomboid.
*Shape of apex.*—Acute.
*Shape of base.*—Truncate.
*Texture.*—Smooth.
*Pubescence.*—Upper surface: Sparse. Lower surface: Dense.
*Aspect.*—Slightly cupped; curved inwardly.
*Margin type.*—Crenate; deeply serrated.
*Color*—Young leaves: Upper surface: 146A. Lower surface: 146B. Mature leaves: Upper surface: 147A. Lower surface: 147B.
*Petioles.*—Length: 0.65 cm. Diameter: 1.3 mm. Color: 146B.
*Veins.*—Arrangement: Pinnate. Color: Upper surface: 147A. Lower surface: 146B.

FLOWER

Natural flowering season: Spring through autumn; tolerate temperatures between 4° C. to 30° C.
Flower type and habit: Single, salverform; persistent; abundant.
Fragrance: None.
Flower size:
*Length.*—1.1 cm.
*Width.*—2.6 cm.
*Tube length.*—1 cm.
*Tube diameter.*—Base: 2 mm. Top: 5 mm.
Aspect: Slightly cupped.
Corolla:
*Petal length from throat.*—11 mm.
*Petal width.*—9 mm.
*Petal quantity.*—5, fused; slightly laciniate.
*Petal shape.*—Rounded.
*Petal apex.*—Obtuse.
*Petal margin.*—Entire.
*Texture.*—Smooth.
*Appearance.*—Dull.
Color:
*Petals.*— *When opening: Upper surface: Lighter than* 155D. Lower surface: Lighter than 155D. Fully opened: Upper surface: Lighter than 155D. Lower surface: Lighter than 155D.
*Flower throat inside surface.*—25B.
*Flower eye.*—25B.
*Flower tube.*—Outside: Top: 155D. Middle: Between 21A and 21B. Base: Between 145C and 145D. Veins: Not veined.
Calyx:
*Arrangement.*—Whorled.
*Sepals.*—Quantity: 5; fused. Shape: Linear. Width: 1.5 mm. Length: 8.7 mm. Margin: Entire. Apex: Acute. Texture: Leathery; pubescent. Appearance: Dull. Color: Upper surface: Varies between 146A and 146B. Lower surface: Varies between 146A and 146B.
Bud:
*Shape.*—Oblanceolate.
*Length.*—0.9–1.0 cm.
*Diameter.*—0.4 cm.
*Color.*—Top: Varies between 157A and 154D. Middle: Varies between 157A and 154D. Base: Varies between 157A and 154D.
*Quantity.*—Abundant.
Peduncle:
*Length.*—9 mm.
*Diameter.*—0.9 mm.
*Color.*—Between 146A and 146B.
*Orientation.*—Acute angle.
*Strength.*—Flexible.

REPRODUCTIVE ORGANS

Stamens:
*Number.*—4; on two plains (2 high, 2 low); fused with petals.
*Filament length.*—Short: 3.5 mm. Long: 5.1 mm.
*Anthers.*—Shape: Flat, reniform. Length: 1.1 mm. Width: 1.5 mm. Color: 21B.
*Pollen.*—Color: 21B. Amount: Abundant.
Pistil:
*Quantity.*—1.
*Length.*—1.25 cm.
*Style.*—Length: 0.9 cm. Color: 145C.
*Stigma.*—Shape: Ovate; narrow. Color: 144A. Ovary color: 143C.
Seeds: Generally none.
Disease/pest resistance: No susceptibility to diseases or pests has been noted to date.

I claim:

1. A new and distinct variety of Sutera plant substantially as shown and described.

* * * * *